(12) United States Patent
Kubosaki et al.

(10) Patent No.: US 11,683,885 B2
(45) Date of Patent: Jun. 20, 2023

(54) SHEET-LIKE DEVICE AND MANUFACTURING METHOD OF THE SAME

(71) Applicant: NISSHA CO., LTD., Kyoto (JP)

(72) Inventors: Nobuo Kubosaki, Kyoto (JP); Chuzo Taniguchi, Kyoto (JP); Jun Sasaki, Kyoto (JP)

(73) Assignee: NISSHA CO., LTD., Kyoto (JP)

( * ) Notice: Subject to any disclaimer, the term of this patent is extended or adjusted under 35 U.S.C. 154(b) by 0 days.

(21) Appl. No.: 17/759,156

(22) PCT Filed: Dec. 2, 2020

(86) PCT No.: PCT/JP2020/044879
§ 371 (c)(1),
(2) Date: Jul. 20, 2022

(87) PCT Pub. No.: WO2021/149363
PCT Pub. Date: Jul. 29, 2021

(65) Prior Publication Data
US 2023/0067899 A1     Mar. 2, 2023

(30) Foreign Application Priority Data

Jan. 21, 2020   (JP) .............................. JP2020-007196

(51) Int. Cl.
*H05K 1/02* (2006.01)
*H05K 1/03* (2006.01)
*G06F 1/16* (2006.01)

(52) U.S. Cl.
CPC ............ *H05K 1/038* (2013.01); *G06F 1/163* (2013.01); *H05K 2201/10098* (2013.01); *H05K 2201/10106* (2013.01); *H05K 2201/10151* (2013.01)

(58) Field of Classification Search
CPC ........ H05K 1/038; H05K 1/182; H05K 1/028; H05K 1/0313; H05K 1/036; H05K 1/0366;
(Continued)

(56) References Cited

U.S. PATENT DOCUMENTS 11,280,685 B2 *  3/2022  Mullen .................. H05K 1/167
2017/0179014 A1 *  6/2017  Tago ..................... H01L 23/642
(Continued)

FOREIGN PATENT DOCUMENTS

JP          H11507765 A    7/1999
JP          2006165892 A   6/2006
(Continued)

*Primary Examiner* — Hoa C Nguyen
(74) *Attorney, Agent, or Firm* — Alleman Hall Creasman & Tuttle LLP

(57) ABSTRACT

Provided is a sheet-like device suitable for a flexible electrical product that is robust, highly flexible, and operates stably. The sheet-like device includes a first part where a first film layer, a first conversion unit, and a second film layer overlap, a second part where the first film layer is absent and the second film layer is present, and a third part where the first film layer, a second conversion unit, and the second film layer overlap. The first part the second part, and the third part are arranged side by side in this order in a first direction. A first region including the first part the second part, and the third part has an elongation per unit length greater than an elongation per unit length of the first film layer alone when a same force is applied in the first direction at 20° C.

5 Claims, 15 Drawing Sheets

(58) Field of Classification Search
CPC .......... H05K 2201/10098; H05K 2201/10106; H05K 2201/10151; H05K 2201/10
See application file for complete search history.

(56) References Cited

U.S. PATENT DOCUMENTS

| | | | |
|---|---|---|---|
| 2018/0184528 A1* | 6/2018 | Pu | ........................ H05K 1/0216 |
| 2018/0192948 A1* | 7/2018 | Okumura | ............... H05K 1/189 |
| 2019/0294004 A1* | 9/2019 | Hashimoto | ......... H01L 25/0753 |
| 2020/0281073 A1* | 9/2020 | Okimoto | ................ H05K 1/189 |
| 2020/0404778 A1* | 12/2020 | Hanazawa | ........... H05K 1/0277 |
| 2021/0045249 A1* | 2/2021 | Tuominen | .............. H05K 1/118 |

FOREIGN PATENT DOCUMENTS

| | | | |
|---|---|---|---|
| JP | 2016063011 A | 4/2016 |
| JP | 2017152687 A | 8/2017 |
| JP | 2019025838 A | 2/2019 |
| JP | 2019043024 A | 3/2019 |
| WO | 2015152060 A1 | 10/2015 |
| WO | 2016059927 A1 | 4/2016 |

* cited by examiner

SHEET-LIKE DEVICE AND MANUFACTURING METHOD OF THE SAME

TECHNICAL FIELD

The present invention relates to a sheet-like device including a film layer that contains a thermoplastic elastomer as a main material and a manufacturing method of the same.

BACKGROUND ART

In recent years, wearable electrical products have been actively developed as wearable devices that are worn by people. Flexibility is required for the wearable electrical products. Example of the wearable electrical products include a wearable electrical product that incorporates a function of blood pressure measurement and/or a function of pulse measurement in a wristband, and a wearable electrical product that incorporates a mobile phone terminal in a glove as described in Patent Document 1.

CITATION LIST

Patent Literature

Patent Document 1: JP 2006-165892 A

SUMMARY OF INVENTION

Technical Problem

When a wearable electrical product is incorporated in a glove as described in Patent Document 1, a component that is robust and operates stably in response to complicated and strenuous movements of the glove is required. The robust component is a component that is less likely to fail when being worn for use. However, there are a variety of required robustness according to an application, for example, a component that can withstand bending a large number of times, a component that can withstand large stress, and a component that is highly waterproof. Also, examples of the stable operation include a stable conversion between a physical quantity of a sensor and an electrical amount, stability of emission of a light-emitting element, stability of heat generation of a heater, and a stable conversion between a current and a radio wave of an antenna.

Although the glove described in Patent Document 1 seems to be functionally excellent, viewing the drawings of the glove, since the electrical function is incorporated, the glove lacks flexibility, and thus wearing comfort of the glove is considered to be poor. In addition, for example, considering that a touch sensor is incorporated in the glove, with the touch sensor that converts a capacitance to an electric amount, a change in capacitance due to deformation of the glove possibly causes an error.

An object of the present invention is to provide a sheet-like device suitable for a flexible electrical product that is robust, highly flexible, and operates stably.

Solution to Problem

Some aspects will be described below as means to solve the problems. These aspects can be combined arbitrarily as necessary.

A sheet-like device according to an aspect is a sheet-like device that includes a first film layer, a second film layer, and an electrical circuit layer. The first film layer contains a thermoplastic resin as a main material. The second film layer is bonded to the first film layer. The second film layer contains a thermoplastic elastomer that extends more than the thermoplastic resin as a main material. The second film layer has an elongation per unit length greater than an elongation per unit length of the first film layer, at 20° C. The electrical circuit layer includes a first conversion unit having a first conversion function and a second conversion unit having a second conversion function. The electrical circuit layer is bonded to the first film layer. The sheet-like device includes a first part, a second part, and a third part. In the first part, the first film layer, the first conversion unit, and the second film layer overlap. In the second part, the first film layer is absent and the second film layer is present. In the third part, the first film layer, the second conversion unit, and the second film layer overlap. The first part, the second part, and the third part of the sheet-like device are arranged side by side in this order in a first direction on an inside of a surface of the second film layer. In this sheet-like device, a first region including the first part, the second part, and the third part has an elongation per unit length greater than an elongation per unit length of the first film layer alone when a same force is applied in the first direction at 20° C.

In the sheet-like device configured in this manner, the elongation of the first film layer is smaller than the elongation of the second film layer. Therefore, compared with a case where the electrical circuit layer is directly formed on the second film layer, the bonding of the electrical circuit layer on the first film layer further well protects the first conversion function and the second conversion function of the electrical circuit layer by the first film layer, and the first conversion unit and the second conversion unit stably operate. Further, stress applied to the first film layer is reduced by the thermoplastic elastomer of the second part where the first film layer is absent and the second film layer is present. As a result, the electrical circuit layer bonded to the first film layer is protected. Furthermore, the elongation of the first region is configured to be greater than the elongation of the first film layer alone. This allows the sheet-like device to flexibly deform according to deformation of a periphery compared with a case where the elongation of the first region is configured to be equivalent to the elongation of the first film layer alone. As a result, for example, when the sheet-like device is applied to a wearable, a wearing comfort of the wearable is improved.

In the above-described sheet-like device, the electrical circuit layer includes a third conversion unit having a third conversion function. The sheet-like device includes a fourth part and a fifth part. In the fourth part, the first film layer is absent and the second film layer is present. In the fifth part, the first film layer, the third conversion unit, and the second film layer overlap. In the sheet-like device, the first part, the fourth part, and the fifth part are arranged side by side in this order in a second direction different from the first direction on the inside of the surface of the second film layer. A second region including the first part, the fourth part, and the fifth part has an elongation per unit length greater than the elongation per unit length of the first film layer alone when a same force is applied in the second direction. In the sheet-like device configured in this manner, stability of the first to third conversion functions is improved in the second direction as well, in addition to the first direction, and flexibility is improved.

In the sheet-like device described above, the second part may have a substantially same thickness as thicknesses of the first part and the third part. The sheet-like device configured in this manner does not generate a step at a boundary between the first part and the third part and the second part. Thus, stress caused by getting caught on these boundaries is prevented, and damage is less likely to occur.

The above-described sheet-like device may include a decorative layer that is bonded to the second film layer and represents a pattern. In the sheet-like device configured in this manner, a positional relationship between the pattern of the decorative layer and the first conversion unit and the second conversion unit is fixed. As a result, when, for example, the sheet-like device is applied to the wearable, even when the sheet-like device deforms due to a movement of a body, arranged locations of the first conversion unit and the second conversion unit can be accurately identified by the decorative layer.

A manufacturing method of a sheet-like device according to an aspect includes bonding an electrical circuit layer including a first conversion unit having a first conversion function and a second conversion unit having a second conversion function to a first film layer containing a thermoplastic resin as a main material to form a circuit film, forming a second film layer containing a thermoplastic elastomer extending more than the thermoplastic resin as a main material and extending more than the first film layer at 20° C. and an elastomer film including a protective film, overlapping the circuit film and the elastomer film and performing a heat press, and peeling the protective film. The performing of the heat press of the manufacturing method of the sheet-like device includes bonding the first film layer and the second film layer while a mold is pressed against the second film layer via the protective film to form irregularities on a surface of the second film layer, and arranging a first part where the first film layer, the first conversion unit, and the second film layer overlap, a third part where the first film layer, the second conversion unit, and the second film layer overlap, and a second part where the first film layer is absent and the second film layer is present side by side in an order of the first part, the second part, and the third part in the first direction on an inside of a surface of the second film layer.

In the sheet-like device manufactured by the manufacturing method of the sheet-like device configured in this manner, the first film layer has the elongation smaller than that of the second film layer. Thus, compared with the case where the electrical circuit layer is formed on the second film layer, the bonding of the electrical circuit layer on the first film layer further well protects the first conversion function and the second conversion function of the electrical circuit layer by the first film layer, and the first conversion unit and the second conversion unit stably operate. Further, stress applied to the first film layer is reduced by the thermoplastic elastomer of the second part where the first film layer is absent and the second film layer is present. As a result, the electrical circuit layer bonded to the first film layer is protected and operates stably. Furthermore, the elongation of the first region is configured to be greater than the elongation per unit length of the first film layer alone. Therefore, compared with the case where only the elongation equivalent to the elongation per unit length of the first film layer alone is obtained, for example, when the sheet-like device is applied to a wearable, flexibility is improved and the sheet-like device further well fits to a movement of a human body. As a result, for example, when the sheet-like device is applied to the wearable, a wearing comfort when the wearable including the sheet-like device is worn is improved. Since the irregularities are formed on the second film layer while being protected by the protective film, deterioration of the surface of the sheet-like device can be prevented. In the manufacturing method of such a sheet-like device, compared with forming the irregularities on the surface of the sheet-like device in a step different from the step of performing heat press on the surface of the sheet-like device, the number of steps of the manufacturing process can be reduced.

The method of manufacturing the sheet-like device described above may include forming a decorative layer on which a pattern is represented between the protective film and the second film layer. The manufacturing method of the sheet-like device configured in this manner allows facilitating positioning between the arranged locations of the first conversion unit and the second conversion unit and the arranged location of the pattern.

Advantageous Effects of Invention

Application of the sheet-like device of the present invention to a flexible electrical product helps improve robustness, flexibility, and operation stability of the electrical product. The manufacturing method of the sheet-like device of the present invention is suitable for manufacturing a decorated sheet-like device.

DESCRIPTION OF EMBODIMENTS

First Embodiment

(1) OVERALL CONFIGURATION

Figure 1:
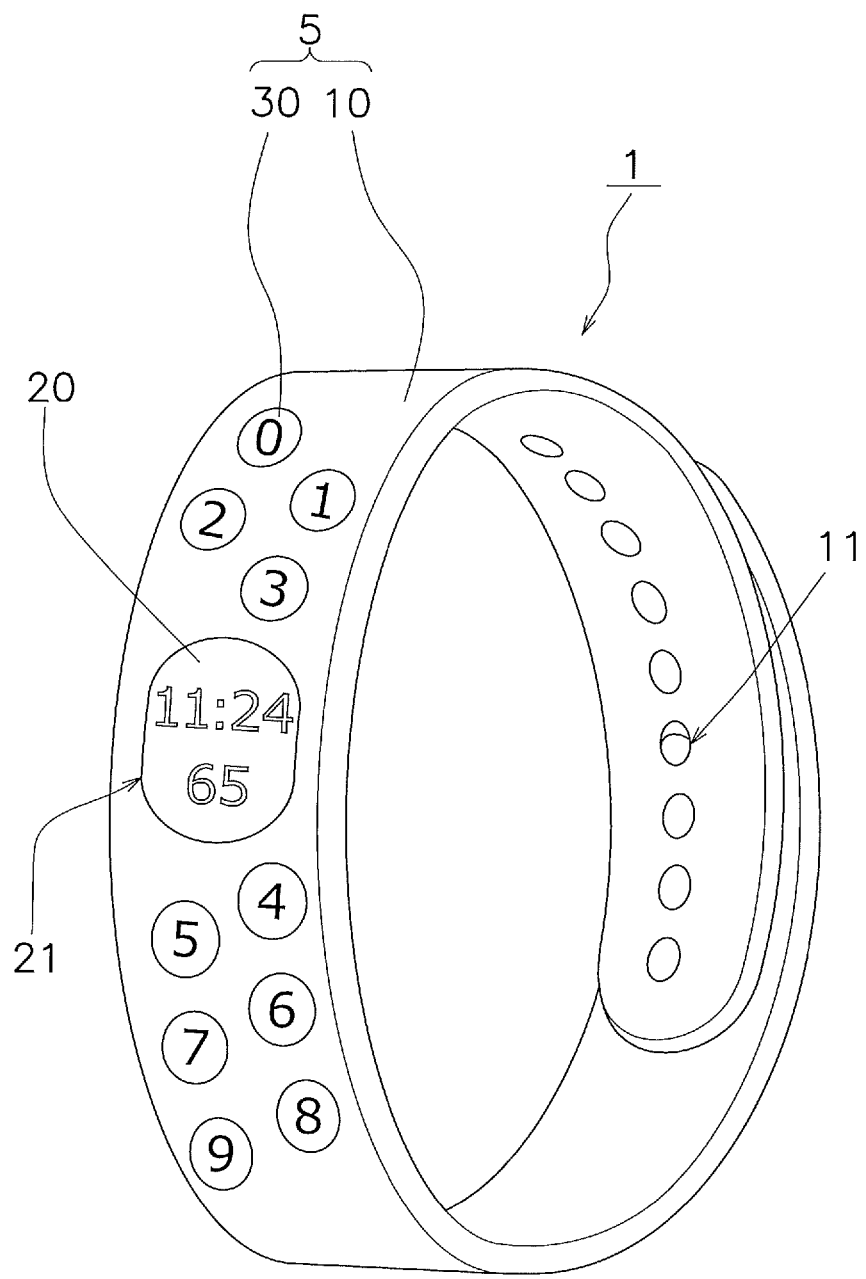
FIG. 1 is a perspective view of a wristband to which a sheet-like device according to a first embodiment is applied.
Figure 2:
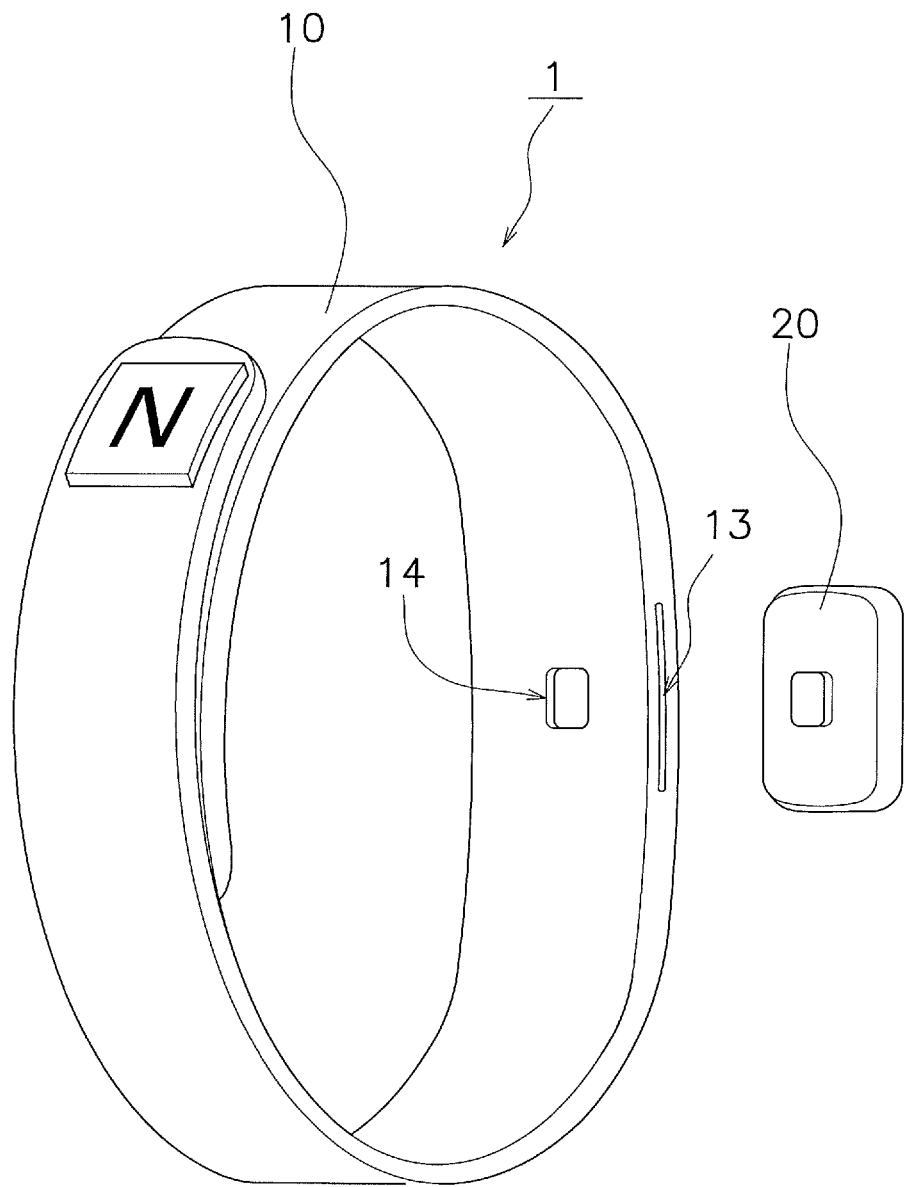
FIG. 2 is a perspective view of a wristband to which the sheet-like device according to the first embodiment is applied.

FIG. 1 and FIG. 2 illustrate a wristband 1 in which a sheet-like device 5 according to a first embodiment is incorporated. The wristband 1 is a decorative product used by being wound around a wrist of a user. A main body portion 10 of the wristband 1 is mainly made of resin and an elastomer, and is configured to be elastically deformable in a longitudinal direction. The wristband 1 includes a locking portion 11 in which a projection is fitted into a hole for fixation. Although the holes of the wristband 1 are provided in an intermittent manner, the main body portion 10 of the wristband 1 deforms, and thus the wristband 1 can be mounted so as to fit to the wrist of a person. For the mounting so as to fit, elongation of the wristband 1 in the longitudinal direction (a first direction D1 indicated in FIG. 3 and FIG. 4) is especially important. The wristband 1 illustrated in FIG. 1 includes a pulse measurement device 20 and a touch sensor 30. In this embodiment, the sheet-like device 5 includes the main body portion 10 and the touch sensor 30.

The pulse measurement device 20 has a function of measuring a pulse of the person wearing the wristband 1 and a clock function. The pulse measurement device 20 includes a display unit 21 that displays the pulse and a time. The display unit 21 of FIG. 1 shows that the pulse for one minute is "65" and the current time is "11:24."

The main body portion 10 of the wristband 1 is provided with a storage unit 13 that stores the pulse measurement device 20. The pulse measurement device 20 having a thin and generally rectangular parallelepiped appearance can be inserted into the storage unit 13 from a side of the wristband 1. The pulse measurement device 20 inserted into the storage unit 13 is connected to the touch sensor 30. Although not illustrated, the pulse measurement device 20 includes an insertion portion into which the touch sensor 30 is inserted for electrical connection. The touch sensor 30 illustrated in FIG. 1 is an input device for inputting a numerical value of from 0 to 9.

Here, the wristband 1 worn directly is described as an example of a flexible electrical product, but, for example, the sheet-like device according to the present invention may be mounted on a wearable, such as a garment. As a method of mounting the sheet-like device to a garment, for example, there are methods of sewing to a garment, adhesion to a garment, fastening to a garment with a clasp, and pinching between a plurality of fabrics of a garment.

(2) DETAILED CONFIGURATION

(2-1) Description of Configuration of Touch Sensor 30

Figure 3:
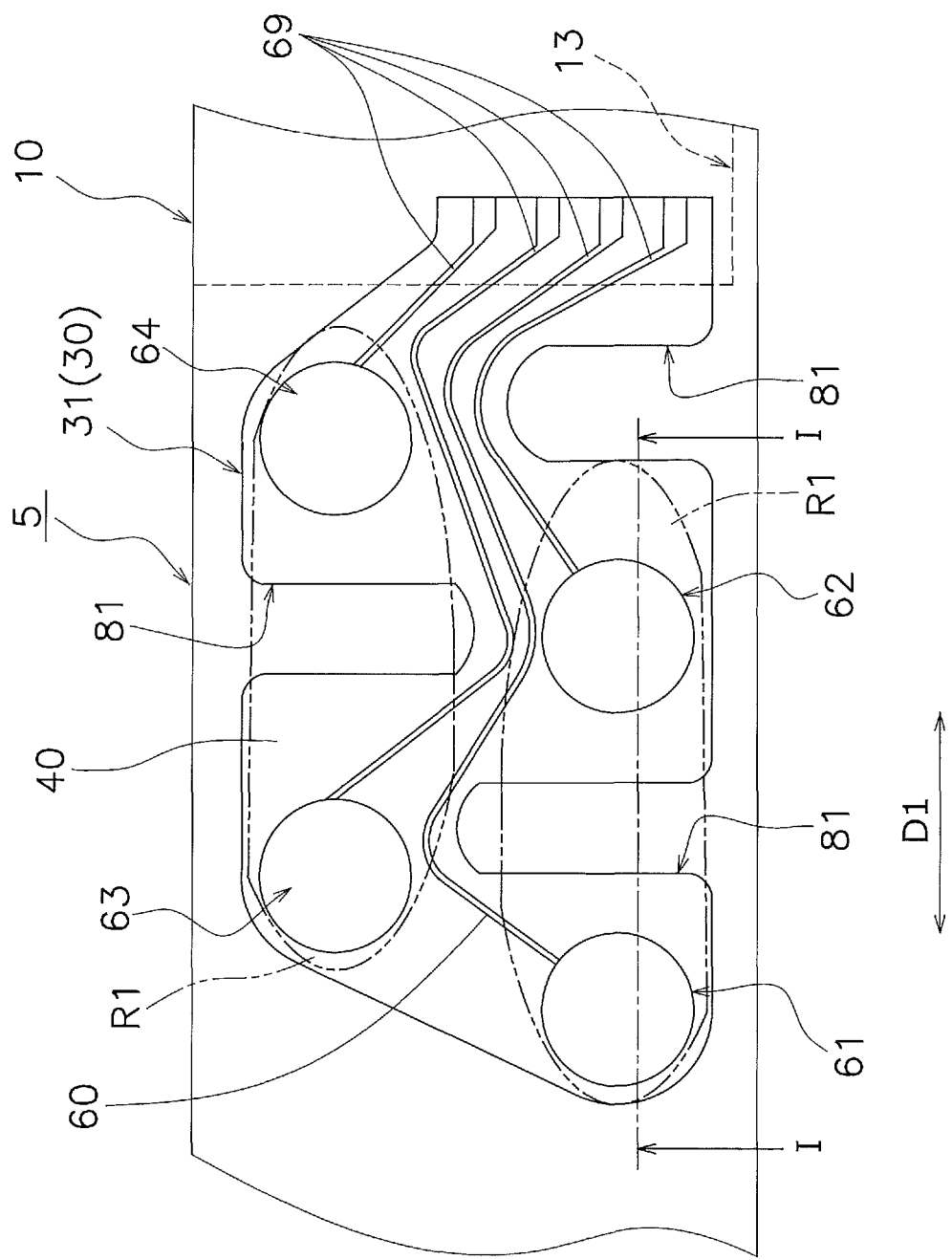
FIG. 3 is a partial enlarged plan view in which a portion of the sheet-like device is enlarged.
Figure 4:
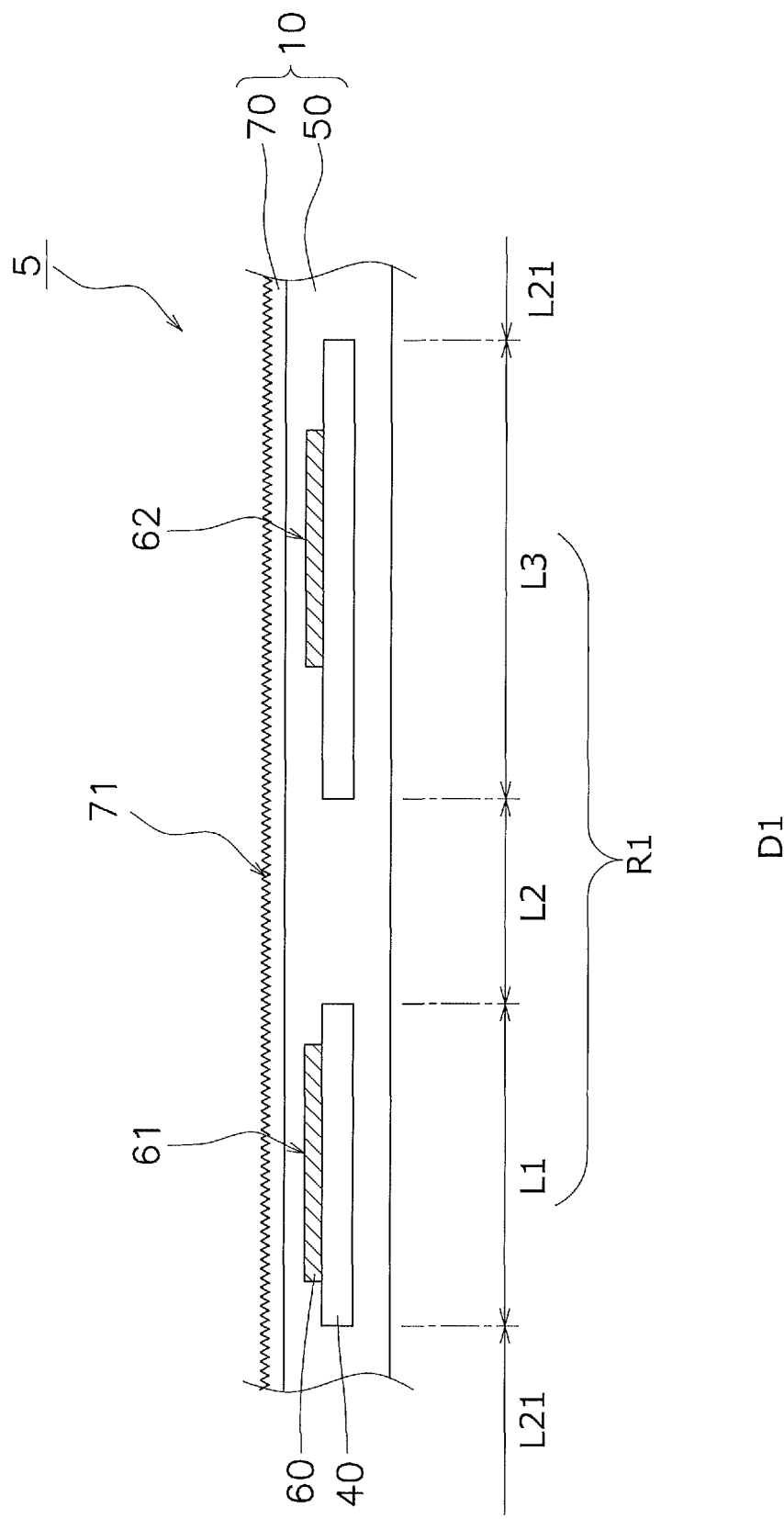
FIG. 4 is a partial cross-sectional view illustrating a cross-sectional surface of the sheet-like device taken along line I-I in FIG. 3.

FIG. 3 and FIG. 4 illustrate an upper portion 31 of the touch sensor 30 for inputting numerical values "0," "1," "2," and "3." FIG. 4 illustrates a cross-sectional surface of the wristband 1 cut along line I-I in FIG. 3. In FIG. 3 and FIG. 4, the longitudinal direction is the first direction D1 indicated by the arrow. As illustrated in FIG. 3 and FIG. 4, the touch sensor 30 is embedded in the main body portion 10 and integrated with the main body portion 10.

The touch sensor 30 includes a first film layer 40 and an electrical circuit layer 60. The main body portion 10 includes a second film layer 50 and a decorative layer 70. In the present invention, the film layer is a thin film-like layer. The thickness of the first film layer 40 is, for example, from 25 µm to 100 µm. The thickness of the second film layer 50 is, for example, from 100 µm to 5 mm. The thickness of the electrical circuit layer 60 is, for example, from 1 µm to 50 µm. The thickness of the decorative layer 70 is, for example, from 5 µm to 100 µm.

The first film layer 40 is a layer containing a thermoplastic resin as a main material. In this description, "as a main material" means that the material accounts for 50% by weight or more of the total. The first film layer 40 contains, for example, polyethylene terephthalate (PET) as a main material. In this case, the first film layer 40 may be made of only polyethylene terephthalate, or a filler may be added in a proportion of 50% by weight or less. For example, the first film layer 40 can be made of 90% by weight of PET and 10% by weight of a filler. Examples of the filler include another thermoplastic resin, thermosetting resin, and an inorganic substance. Examples of the inorganic substance include talc, carbon fiber, and ceramic. Examples of the thermoplastic resin include polyimide (PI), polycarbonate (PC), and polyethylene naphthalate (PEN), in addition to polyethylene terephthalate.

The second film layer 50 is a layer containing a thermoplastic elastomer (TPE) as a main material. The thermoplastic elastomer includes, for example, amide-based TPE (TPA), ester-based TPE (TPC), olefin-based TPE (TPO), styrene-based TPE (TPS), and urethane-based TPE (TPU). The second film layer 50 may also be filled with 50% by weight or less of a filler. The TPE, which is the main material of the second film layer 50, has an elongation per unit length at 20° C. greater than that of the thermoplastic resin, which is the main material of the first film layer 40. Furthermore, the second film layer 50 containing such a thermoplastic elastomer as the main material has an elongation per unit length at 20° C. greater than that of the first film layer 40, which contains the thermoplastic resin as the main material. The second film layer 50 is bonded to the first film layer 40.

The electrical circuit layer 60 includes a first conversion unit 61 having a first conversion function, a second conversion unit 62 having a second conversion function, and wirings 69. The conversion functions in the present invention are functions of performing a conversion between a certain electrical phenomenon and another physical phenomenon other than the electrical phenomenon. The conversion function in this case also includes a function of converting a certain electrical phenomenon into another electrical phenomenon other than the electrical phenomenon. The first conversion unit 61 and the second conversion unit 62 are connected to an external device located outside the electrical circuit layer 60 by the wirings 69. In the first embodiment, the pulse measurement device 20 is the external device connected by the wirings 69. The electrical circuit layer 60 is bonded to the first film layer 40. The first conversion unit 61 has the first conversion function for inputting a numerical value "0," and the second conversion unit 62 has the second conversion function for inputting a numerical value "2." The first conversion function and the second conversion function in this case are functions that convert a change in capacitance into an electrical signal through a contact of a finger of a wearer of the wristband 1 with the main body portion 10 on the first conversion unit 61 or the second conversion unit 62.

In the first embodiment, the case in which the first conversion function and the second conversion function are the functions that convert the change in capacitance into the electrical signal and the sheet-like device 5 includes the touch sensor 30 has been described, but the configuration constituting the sheet-like device is not limited to this type of touch sensor. For example, another sensor other than the touch sensor that converts a physical quantity into an electrical signal can be included in the sheet-like device. Also, the functions that can be used as the first conversion function and the second conversion function include, for example, a light-electricity conversion function, a heat-electricity conversion function, and a radio wave-current conversion function. The light-electricity conversion function includes a function of converting electricity into light and a function of converting light into electricity. A device that achieves the function of converting electricity into light is, for example, a light emitting diode (LED). A device that achieves the function of converting light into electricity is, for example, a solar cell and a photodiode. A device that achieves the heat-electricity conversion function, which converts electricity into heat, is a heater. A device that achieves the radio wave-current conversion function, which performs conversion between a radio wave and a current, is an antenna. In the first embodiment, the case where the first conversion function and the second conversion function are the same conversion function has been described, but the first conversion function and the second conversion function may be different conversion functions. The different conversion functions are, for example, the above-described sensor and the light-electricity conversion function, the sensor and the heat-electricity conversion function, the sensor and radio wave-current conversion function, the light-electricity conversion function and the heat-electricity conversion function, the light-electricity conversion function and the radio wave-current conversion function, and the heat-electricity conversion function and the radio wave-current conversion function. The first conversion unit having the first conversion function and the second conversion unit having the second conversion function allow flowing electricity separately.

As illustrated in FIG. 4, when viewing the cut surface taken along line I-I, the sheet-like device 5 includes a first part L1, a second part L2, and a third part L3. The first part L1, the second part L2, and the third part L3 are arranged side by side in the order in the first direction D1 on the inside of the surface of the second film layer 50. A region including the first part L1, the second part L2, and the third part L3 arranged along the first direction D1 is a first region R1. An elongation per unit length of the first region R1 is configured to be greater than an elongation per unit length of the first film layer 40 alone when the same force is applied in the first direction D1 at 20° C. The elongation per unit lengths of the first part L1 and the third part L3 are substantially the same as the elongation per unit length of the first film layer 40 alone. However, since the elongation per unit length of the second part L2 is greater than the elongation per unit length of the first film layer 40 alone at 20° C., seeing the entire first region R1 as one member, the elongation per unit length of the first region R1 is greater than the elongation per unit length of the first film layer 40 alone at 20° C.

The first part L1 is a portion where the first film layer 40, the first conversion unit 61, and the second film layer 50 overlap. The second part L2 is a portion where the first film layer 40 is absent and the second film layer 50 is present. The third part L3 is a portion where the first film layer 40, the second conversion unit 62, and the second film layer 50 overlap. These first part L1, second part L2, and third part L3 are configured such that the thicknesses are substantially the same.

Additionally, a conversion unit for inputting a numerical value "1" is another conversion unit 63 and a conversion unit for inputting a numerical value "3" is another conversion unit 64. At this time, a portion where the first film layer 40, the conversion unit 63, and the second film layer 50 overlap is equivalent to the first part, and a portion where the first film layer 40, the conversion unit 64, the second film layer 50 overlap is equivalent to the third part, and a portion of a slit 81 between the portions equivalent to the first part and the third part is equivalent to the second part. In this way, a region in which the conversion unit 63 and the conversion unit 64 are arranged is also a region equivalent to the first region R1 in which the first part, the second part, and the third part are arranged in the order along the first direction D1. In this manner, a region like the first region R1 along the first direction D1 may be provided by a plurality of rows.

Focusing on the first conversion unit 61, second parts L2 and L21, which are portions where the first film layer 40 is absent and the second film layer 50 is present, are arranged on both sides of the first conversion unit 61. Such a configuration is similar to the second conversion unit 62 and the conversion units 63 and 64. In this way, when both sides of the first conversion unit 61 are interposed between the portions where the first film layer 40 is absent and the second film layer 50 is present, stress is less likely to transmit from both sides of the first conversion unit 61 to the first conversion unit 61. The second conversion unit 62 and the conversion units 63 and 64 also provide such an effect.

The decorative layer 70 is formed on a front side as a side on which a display unit 12 is arranged among the two main surfaces of the second film layer 50. On the decorative layer 70, a numerical value from "0" to "9" is drawn. For example, the numerical value "0" is arranged at a location overlapping with the first conversion unit 61. As a result, when the wearer of the wristband 1 touches the location on which "0" is drawn of the decorative layer 70, the numerical value "0" can be input to the pulse measurement device 20 by the touch sensor 30.

On the surface of the decorative layer 70, in other words, the surface of the second film layer 50, irregularities 71 are formed. Here, the case in which the irregularities 71 are formed on the front surface of the decorative layer 70 is described, but the irregularities may be formed on the back surface of the second film layer 50, for example. Alternatively, the irregularities 71 of the decorative layer 70 need not be formed. In this wristband 1, not only the irregularities 71 on the surface of the decorative layer 70 function as decoration, but also function as a mark for identifying the front and the back of the wristband 1.

(2-2) Description of Pulse Measurement Device 20

The pulse measurement device 20 is a device connected to the sheet-like device 5. The pulse measurement device 20 is brought into contact with the wearer of the wristband 1 through an opening 14 to measure the pulse. As already described, the pulse measurement device 20 can display the measured pulse for one minute and the time on the display unit 12. The pulse measurement device 20 is connected to the sheet-like device 5, and a numerical value from "0" to "9" can be input by the sheet-like device 5.

For example, in a state in which the pulse measurement device 20 receives the input, when the wearer of the wristband 1 touches the location where the number "0" is drawn with the finger, the numerical value "0" is input to the pulse measurement device 20. When the wearer of the wristband 1, for example, desires to know the pulse at eleven, after changing a mode to a predetermined input mode using the touch sensor 30, inputs numerical values "1," "1," "0," and "0." After the input of the four-digit numerical value, the display unit 12 switches to display, for example, "11:00" and "68" and the wristband 1 informs the wearer of the wristband 1 that the pulse at eleven o'clock is 68 times/minute.

(3) MANUFACTURING METHOD OF SHEET-LIKE DEVICE 5

Figure 7:
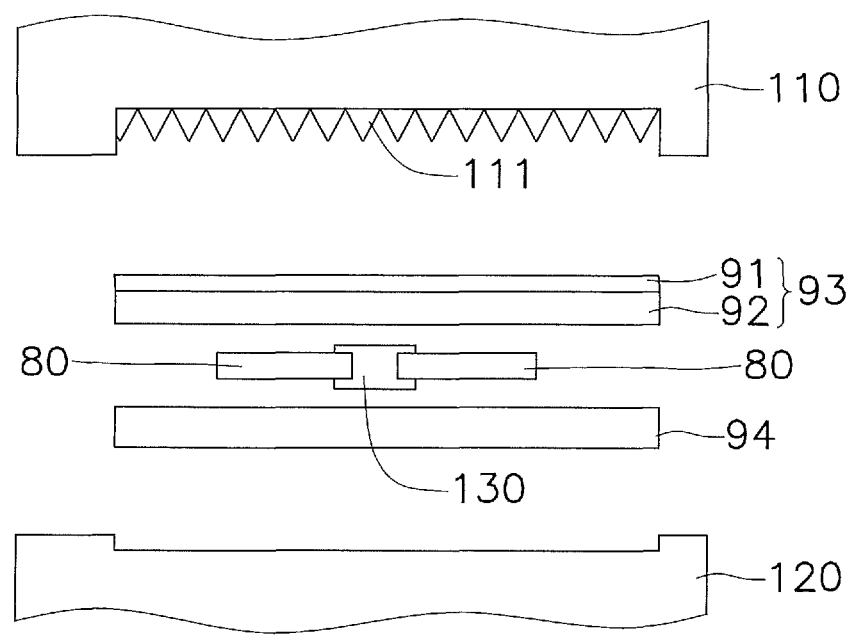
FIG. 7 is a schematic view for describing a step of a thermal bless.

The main part of the sheet-like device 5 is a step of heat press illustrated in FIG. 7. In the step of heat press illustrated in FIG. 7, a first elastomer film 93 and a second elastomer film 94 are arranged on both sides of a circuit film 80.

(3-1) Formation of Circuit Film

The circuit film 80 illustrated in FIG. 7 is a film including the first film layer 40 and the electrical circuit layer 60. An electrical circuit is formed on a resin film and the slit 81 (see FIG. 3) is formed to generate the circuit film 80. The electrical circuit layer 60 functioning as the touch sensor 30 is formed by, for example, etching a metal foil bonded to the first film layer 40. Alternatively, the electrical circuit layer 60 is formed by screen printing of conductive ink, for example. Alternatively, the electrical circuit layer 60 is formed by etching a metal film deposited on the first film layer 40, for example. The slit 81 is formed, for example, by punching by a press. The width of the slit 81 in the first direction D1 is, for example, from 10 mm to 500 mm. Any of the formation of the electrical circuit layer 60 and the formation of the slit 81 may be performed first.

(3-2) Formation of Elastomer Film

Figure 5:
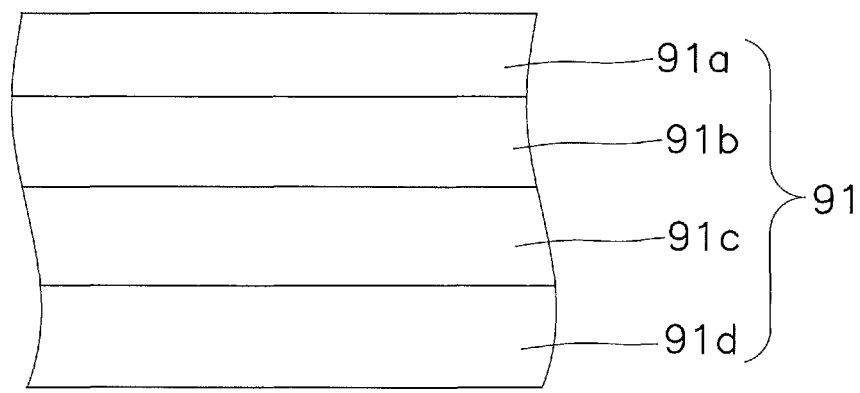
FIG. 5 is a schematic cross-sectional view of a transfer film.

First, a transfer film 91 illustrated in FIG. 5 is prepared. The transfer film 91 includes a carrier film 91a, a top layer 91b, a graphic layer 91c, and an adhesive layer 91d. A PET film having a thickness of, for example, from 25 μm to 100 μm is used for the carrier film 91a. Note that the film used for the carrier film 91a is not limited to the PET film, and may be another resin film.

The top layer 91b has a function to protect the graphic layer 91c and covers the entire graphic layer 91c. The formation of the top layer 91b imparts high durability to the wristband 1. Examples of the material of the top layer 91b include a urethane-based thermoplastic resin. Note that the transfer film 91 can be configured without the top layer 91b.

The graphic layer 91c is a layer on which a graphic is drawn. The materials forming the graphic layer 91c include, for example, resin, such as an acrylic resin, a vinyl chloride vinyl acetate copolymer resin, a thermoplastic urethane resin, or a polyester resin, and a pigment or dye that is added to the resin. The graphic layer 91c may also have a metallic design formed using, for example, an aluminum paste or mirror ink.

The resin used for the adhesive layer 91d includes a urethane resin, a polyester resin, a polyamide resin, an acrylic resin, a vinyl chloride vinyl acetate copolymer resin, and a synthetic rubber. The adhesive layer 91d exhibits adhesiveness by heat, and improves the adhesive strength of the decorative layer 70 and the second film layer 50.

The top layer 91b, the graphic layer 91c, and the adhesive layer 91d are formed by, for example, gravure printing method, a screen printing method, or a transfer method. The top layer is formed, for example, at a thickness of from 1 μm to 10 μm. The graphic layer 91c is formed, for example, at a thickness of from 1 μm to 50 μm. The thickness of the adhesive layer 91d is, for example, from 1 μm to 10 μm.

Figure 6:
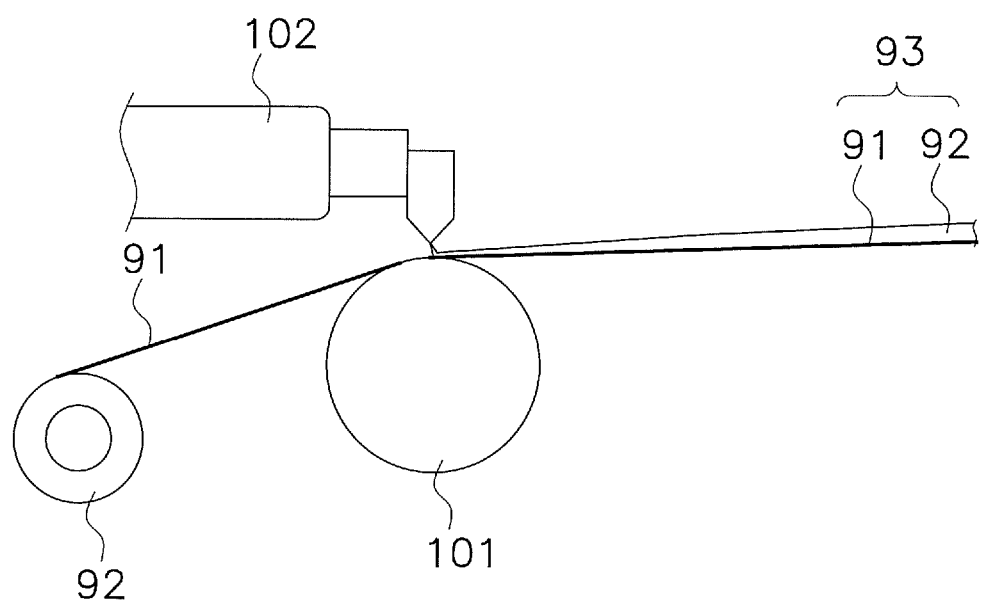
FIG. 6 is a schematic view for describing a manufacturing step of an elastomer film.

As illustrated in FIG. 6, the prepared transfer film 91 is unwound from a wound roll to be supplied. The transfer film 91 is delivered through the surface of a drum 101. A thermoplastic polyurethane elastomer 92 (TPU 92) extruded into a film shape from an extruder 102 is bonded to the transfer film 91 on the drum 101. The TPU 92 is formed so as to contact the adhesive layer 91d. In this manner, the first elastomer film 93 is formed from the transfer film 91 and the TPU 92.

The second elastomer film 94 (see FIG. 7) for forming the back surface of the wristband 1 is a film made of only TPU, and thus description of the formation method is omitted.

(3-3) Description of Heat Press

In the step of performing the heat press, as illustrated in FIG. 7, the circuit film 80, the first elastomer film 93, and the second elastomer film 94 are stacked, and the heat press is performed. To perform the heat press, between a first mold 110 and a second mold 120, the first elastomer film 93, the circuit film 80, and the second elastomer film 94 are arranged in the order closer to the first mold 110. The first mold 110 has irregularities 111 for forming the irregularities 71 provided on the surface of the wristband 1. Here, a spacer 130 for forming the storage unit 13 is arranged so as to be stacked together with the circuit film 80. The shape of the spacer 130 is, for example, a shape of imitating the appearance of the pulse measurement device 20. The spacer 130 may be a slide core of a mold including the first mold 110 and the second mold 120. The heat press is performed for 10 minutes at 150° C., for example.

(3-4) Removal of Carrier Film

Figure 8:
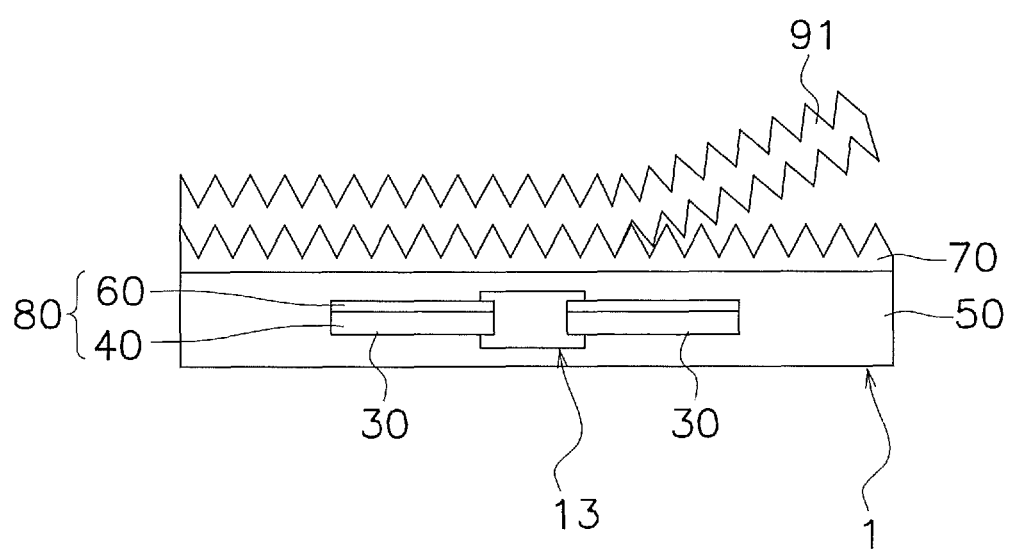
FIG. 8 is a schematic cross-sectional view of a sheet-like device for describing a step of removing a carrier film.

As illustrated in FIG. 8, after the heat press ends, the carrier film 91a is peeled. FIG. 8 schematically illustrates the cross-sectional shape of the wristband 1. Pressing the first mold 110 from above the carrier film 91a during heat press suppresses a defect during heat press, such as a flaw of the wristband 1. After the end of heat press, the spacer 130 is also removed. In this embodiment, using the carrier film 91a as a protective film, the used amount of the protective film is reduced.

Second Embodiment

In the first embodiment, the sheet-like device 5 including the first region R1 in which the portion where the first film layer 40, the first conversion unit 61, and the second film layer 50 overlap (for example, the first part L1), the portion where the first film layer 40 is absent and the second film layer 50 is present (for example, the second part L2), and the portion where the first film layer 40, the second conversion unit 62, and the second film layer 50 overlap (for example, the third part L3) are arranged in the order only in the first direction D1 has been described. However, the three parts as described above may be arranged in a plurality of directions.

Figure 9:
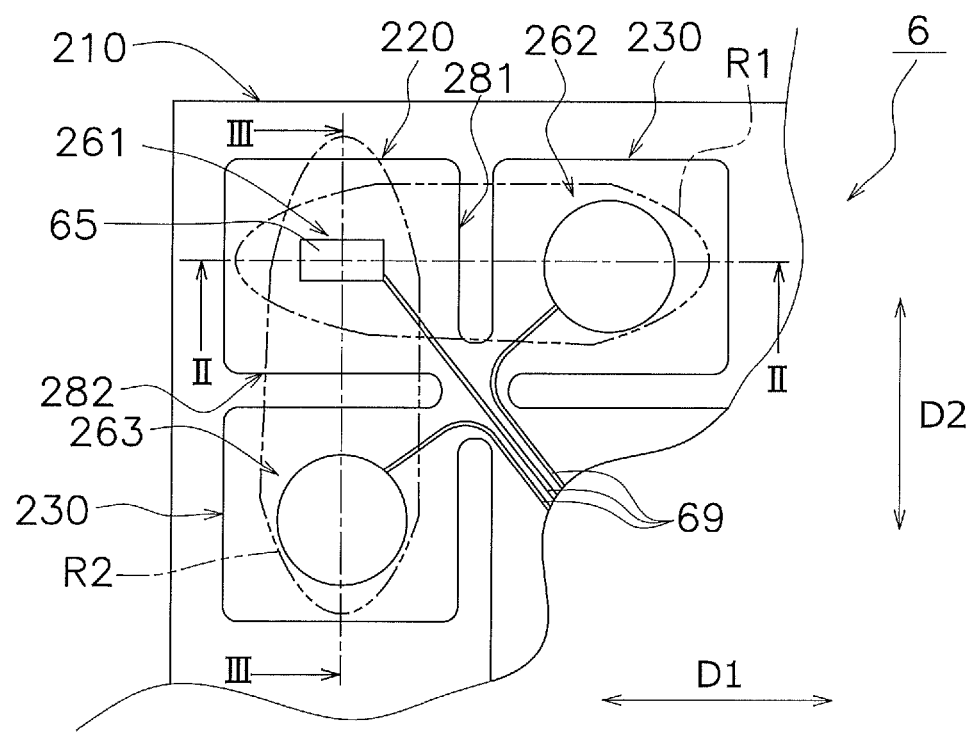
FIG. 9 is a partial enlarged plan view in which a portion of a sheet-like device according to a second embodiment is enlarged.

In a second embodiment, as illustrated in FIG. 9, two directions, the first direction D1 and a second direction D2, a direction orthogonal to the first direction D1, will be considered.

(4) CONFIGURATION OF SHEET-LIKE DEVICE

Figure 10:
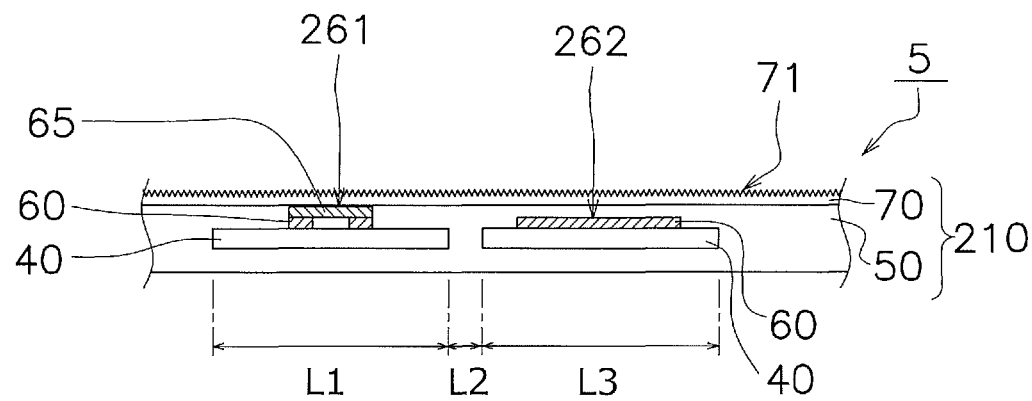
FIG. 10 is a partial cross-sectional view illustrating a cross-sectional surface of the sheet-like device taken along line II-II in FIG. 9.
Figure 11:
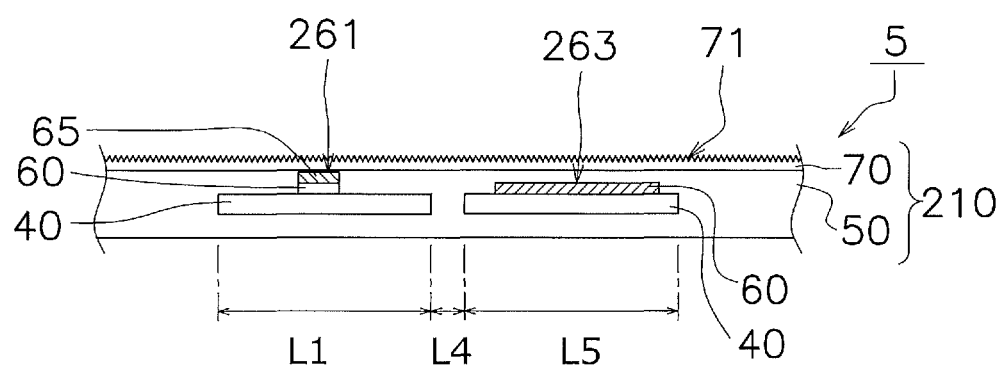
FIG. 11 is a partial cross-sectional view illustrating a cross-sectional surface of the sheet-like device taken along line in FIG. 9.

FIG. 9 illustrates a portion of a sheet-like device 6 according to the second embodiment. The sheet-like device 6 illustrated in FIG. 9 includes a main body portion 210, a light-emitting unit 220, and a touch sensor 230. FIG. 10 illustrates a cross-sectional surface of the sheet-like device 6 cut along line II-II in FIG. 9, and FIG. 11 illustrates a cross-sectional surface of the sheet-like device 6 cut along line in FIG. 9. The light-emitting unit 220 and the touch sensor 230 include the first film layer 40 and the electrical circuit layers 60. The electrical circuit layer 60 of the light-emitting unit 220 includes an LED element 65. As illustrated in FIG. 9 to FIG. 11, the light-emitting unit 220 and the touch sensor 230 are embedded in the main body portion 210 and integrated with the main body portion 210. The main body portion 210 includes the second film layer 50 and the decorative layer 70. On the surface of the decorative layer 70, the irregularities 71 are formed.

The electrical circuit layer 60 includes a first conversion unit 261 having a first conversion function, a second conversion unit 262 having a second conversion function, a third conversion unit 263 having a third conversion function, and the wirings 69. The first conversion unit 261, the second conversion unit 262, and the third conversion unit 263 are connected to an external device located outside the electrical circuit layer 60 by the wirings 69.

The electrical circuit layer 60 is bonded to the first film layer 40. The first conversion unit 261 of the second embodiment has the first conversion function that converts electricity into light. The second conversion unit 262 and the third conversion unit 263 have functions that convert a change in capacitance into an electrical signal through a contact of a finger of a wearer of the sheet-shaped device 6 with the main body portion 210 on the second conversion unit 262 or the third conversion unit 263.

Although the description has been given with an example of the function of converting electricity into light as the first conversion function in the second embodiment, for example, the first conversion function may be a sensor function that converts a physical quantity into an electrical signal, a heat-electricity conversion function, or a radio wave-current conversion function. Also, the case in which the second conversion function and the third conversion function are the functions of converting the change in capacitance into the electrical signal and the sheet-like device 6 includes the touch sensor 230 has been described, but the configuration constituting the sheet-like device is not limited to the touch sensor. For example, another sensor other than the touch sensor that converts a physical quantity into an electrical signal can be included in the sheet-like device. Also, the functions that can be used as the second conversion function and the third conversion function include, for example, a light-electricity conversion function, a heat-electricity conversion function, and a radio wave-current conversion function.

Further, in the second embodiment, the case in which the second conversion function and the third conversion function are the same function is described, but the second conversion function and the third conversion function may be different functions. In the second embodiment, the case in which the first conversion function is different from the second conversion function and the third conversion function has been described, but the first conversion function, the second conversion function, and the third conversion function may be the same.

When viewing the cross-sectional surface (see FIG. 10) taken along line II-II illustrated in FIG. 9, the sheet-like device 6 includes the first part L1, the second part L2, and the third part L3. The first part L1, the second part L2, and the third part L3 are arranged side by side in the order in the first direction D1 on the inside of the surface of the second film layer 50. A region including the first part L1, the second part L2, and the third part L3 arranged along the first direction D1 is the first region R1. An elongation per unit length of the first region R1 of the sheet-like device 6 is configured to be greater than an elongation per unit length of the first film layer 40 alone when the same force is applied in the first direction D1 at 20° C. The first part L1 of the second embodiment is a portion where the first film layer 40, the first conversion unit 261, and the second film layer 50 overlap. The second part L2 is a portion where the first film layer 40 is absent and the second film layer 50 is present. The third part L3 is a portion where the first film layer 40, the second conversion unit 262, and the second film layer 50 overlap. These first part L1, second part L2, and third part L3 are configured such that the thicknesses are substantially the same. Forming a first slit 281 in the first film layer 40 provides the second part L2. The first slit 281 extends along the second direction D2 from the end portion of the first film layer 40.

When viewing the cross-sectional surface (see FIG. 11) taken along line illustrated in FIG. 9, the sheet-like device 6 includes the first part L1, a fourth part L4, and a fifth part L5. The first part L1, the fourth part L4, and the fifth part L5 are arranged side by side in the order in the second direction D2 on inside of the surface of the second film layer 50. A region including the first part L1, the fourth part L4, and the fifth part L5 arranged along the second direction D2 is a second region R2. An elongation per unit length of the second region R2 of the sheet-like device 6 is configured to be greater than an elongation per unit length of the first film layer 40 alone when the same force is applied in the second direction D2 at 20° C.

The fourth part L4 of the second embodiment is a portion where the first film layer 40 is absent and the second film layer 50 is present. The fifth part L5 is a portion where the first film layer 40, the third conversion unit 263, and the second film layer 50 overlap. These first part L1, fourth part L4, and fifth part L5 are configured such that the thicknesses are substantially the same. Forming a second slit 282 in the first film layer 40 provides the fourth part L4. The second slit 282 extends along the first direction D1 from the end portion of the first film layer 40.

Focusing on the first conversion unit 261, excluding a portion of the first conversion unit 261, four sides of the first conversion unit 261 are surrounded by a portion where the first film layer 40 is absent and the second film layer 50 is present. In other words, 90% or more of the periphery of the first conversion unit 261 is surrounded by a portion where the first film layer 40 is absent and the second film layer 50 is present. The same applies to the second conversion unit 262 and the third conversion unit 263. Thus, when 90% or more of the periphery of the first conversion unit 261 is surrounded by the portion where the first film layer 40 is absent and the second film layer 50 is present, stress is less likely to be transmitted from the periphery of the first conversion unit 261 to the first conversion unit 261. The second conversion unit 262 and the third conversion units 263 also provide such an effect.

The decorative layer 70 is formed on the surface of the second film layer 50 closer to the LED element 65 among the two main surfaces. For example, a display related to the second conversion unit 262 and the third conversion unit 263 is drawn in the decorative layer 70. On the surface of the decorative layer 70, the irregularities 71 are formed. Here, the case in which the irregularities 71 are formed on the front surface of the decorative layer 70 is described, but the irregularities may be formed on the back surface of the second film layer 50, for example. Alternatively, the irregularities 71 of the surface of the decorative layer 70 need not be formed.

Similar to the manufacturing method of the sheet-like device 5 according to the first embodiment, the sheet-like device 6 according to the second embodiment can also be configured by including the step of forming the circuit film, the step of forming the elastomer film, the step of performing the heat press, and the step of peeling the carrier film, which is the protective film.

(5) MODIFIED EXAMPLES (5-1) First Modified Example

Except for the sheet-like device 5 of the first embodiment or the sheet-like device 6 of the second embodiment, the sheet-like device can have various shapes. Examples of shapes of other sheet-like devices 7A to 7D are illustrated in FIG. 12 to FIG. 15.

Figure 12:
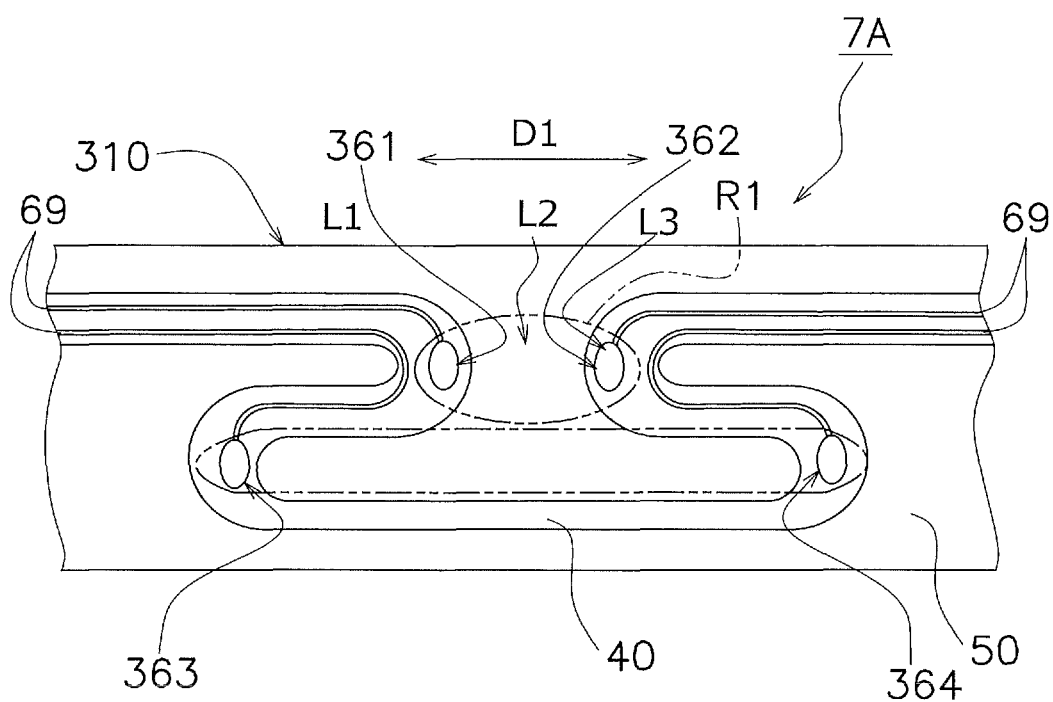
FIG. 12 is a partially enlarged plan view illustrating an example of a sheet-like device according to a modified example.

The sheet-like device 7A illustrated in FIG. 12 includes a main body portion 310 extending long in a band-like shape in the first direction D1. The first film layer 40 has a shape of joining an S-shape and a reverse S-shape together. The second film layer 50 has a band-like shape extending along the first direction D1. In the sheet-like device 7A illustrated in FIG. 12, the first region R1 is formed in a region including a first conversion unit 361 and a second conversion unit 362. In the sheet-like device 7A, a region equivalent to the first region R1 is also formed in a region including another set of other conversion units 363 and 364. In the sheet-like device 7A, the wirings 69 connected to the first conversion unit 361 and the other conversion unit 363 are separated from the wirings 69 connected to the second conversion unit 362 and the other conversion unit 364, and thus the wirings 69 are less likely to be cut even when the sheet-like device 7A repeats stretch in the first direction D1.

Figure 13:
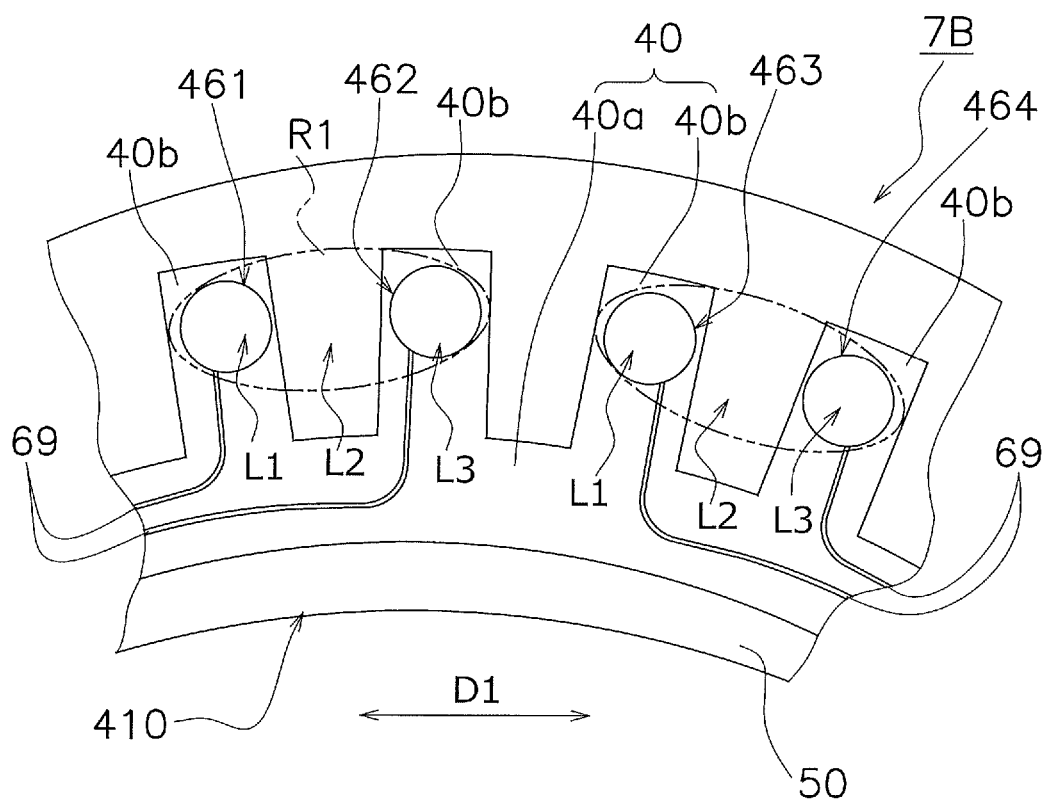
FIG. 13 is a partially enlarged plan view illustrating another example of a sheet-like device according to a modified example.

The sheet-like device 7B illustrated in FIG. 13 has a main body portion 410 that extends long in the first direction D1. The state of the main body portion 410 illustrated in FIG. 13 gently curves along the first direction D1. In the main body portion 410 of FIG. 13, a force of curving the main body portion 410 is applied. Removal of this force returns the main body portion 410 to the shape extending straight along the first direction D1. The first film layer 40 includes a trunk portion 40*a* that extends linearly along the first direction and a plurality of branch portions 40*b*. Each of the branch portions 40*b* extends in a direction intersecting with the trunk portion 40*a*, and more specifically, in a direction orthogonal to the trunk portion 40*a*. The second film layer 50 has a band-like shape extending along the first direction D1. In the sheet-like device 7B illustrated in FIG. 13, the first region R1 is formed in a region including a first conversion unit 461 and a second conversion unit 462. In the sheet-like device 7B, a region equivalent to the first region R1 is also formed in a region including another set of other conversion units 463 and 464. In the sheet-like device 7A, the wirings 69 connected to the first conversion unit 461 and the other conversion unit 463 are separated from the wirings 69 connected to the second conversion unit 462 and the other conversion unit 464, and thus the wirings 69 are less likely to be cut even when the sheet-like device 7B repeatedly curves and returns to a linear shape in the first direction D1.

Figure 14:
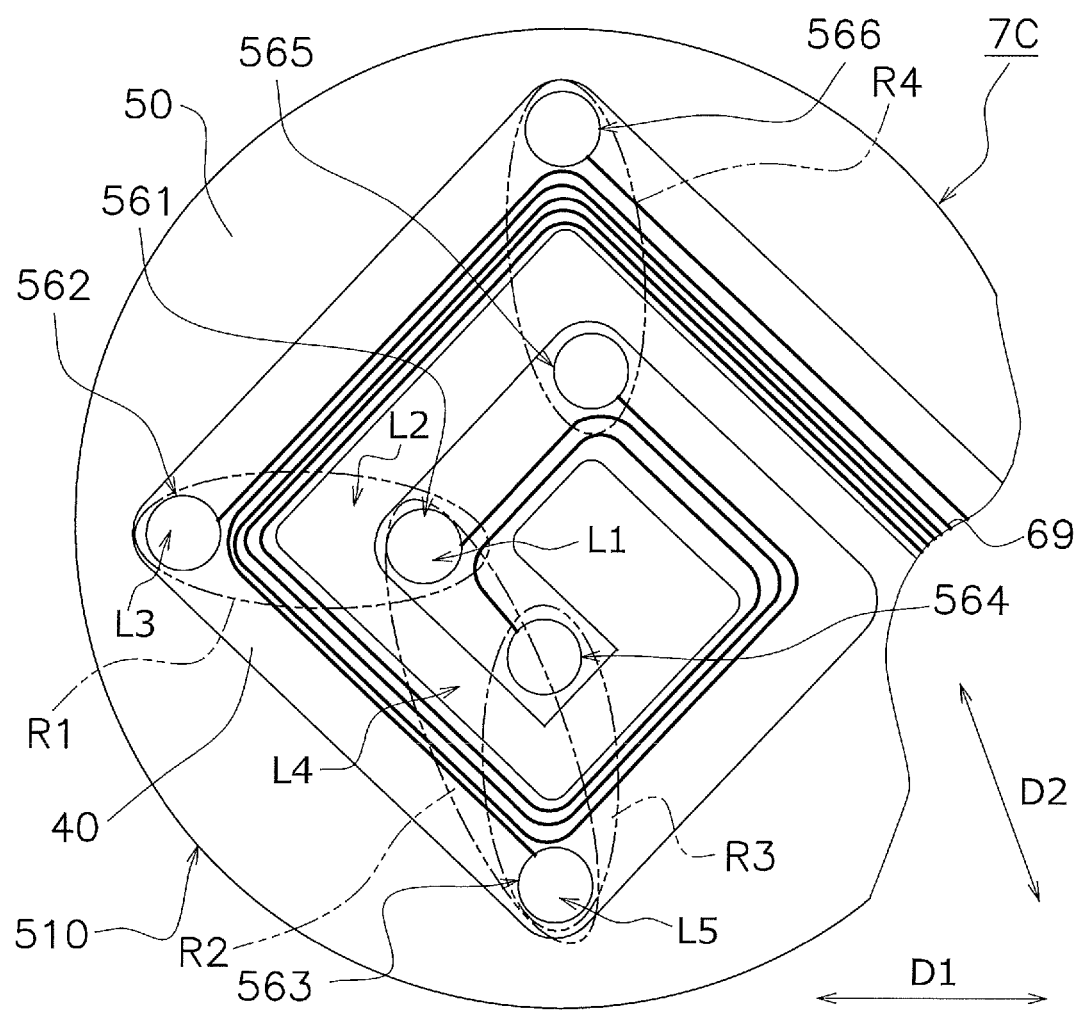
FIG. 14 is a partially enlarged plan view illustrating another example of a sheet-like device according to a modified example.

The sheet-like device 7C illustrated in FIG. 14 includes a disk-shaped main body portion 510. The main body portion 510 has the disk shape, and thus expands both in the first direction D1 and the second direction D2. The first film layer 40 has a spiral shape. Here, although the spiral is formed so as to bend the straight portion, the spiral shape can be formed with, for example, only a curved line. The second film layer 50 has a disk shape. In the sheet-like device 7C illustrated in FIG. 14, the first region R1 is formed in a region including a first conversion unit 561 and a second conversion unit 562. In the sheet-like device 7C, the second region R2 including the first conversion unit 561 and a third conversion unit 563 is formed.

The sheet-like device 7C has a structure in which the sheet-like device 7C easily stretches also in a direction perpendicular to an in-plane direction that the disk-shaped main body portion 510 stretches, in addition to the first direction D1 and the second direction D2. When the main body portion 510 thus easily stretches also in the direction perpendicular to the in-plane direction, application to a location that moves so as to protrude with respect to its periphery, such as an elbow, a knee, and a shoulder, is easy.

Note that in FIG. 14, in the sheet-like device 7C, the first part, the second part, and the third part are arranged in the first direction D1, and the first part, the fourth part, and the fifth part are arranged in the second direction D2. However, as a region in which the portion where the first film layer 40, the conversion unit, and the second film layer 50 overlap, the portion where the first film layer 40 is absent and the second film layer 50 is present, and the portion where first film layer 40, the other conversion unit, and the second film layer 50 overlap are arranged in the order, another region in which they are arranged along, not only in the first direction D1 or the second direction D2, but also in a direction other than the first direction D1 or the second direction D2 may be provided. As the other region, for example, in the sheet-like device 7C, a third region R3 including the third conversion unit 563 and a fourth conversion unit 564 is formed, and a fourth region R4 including another set of a fifth conversion unit 565 and a sixth conversion unit 566 is formed.

Figure 15:
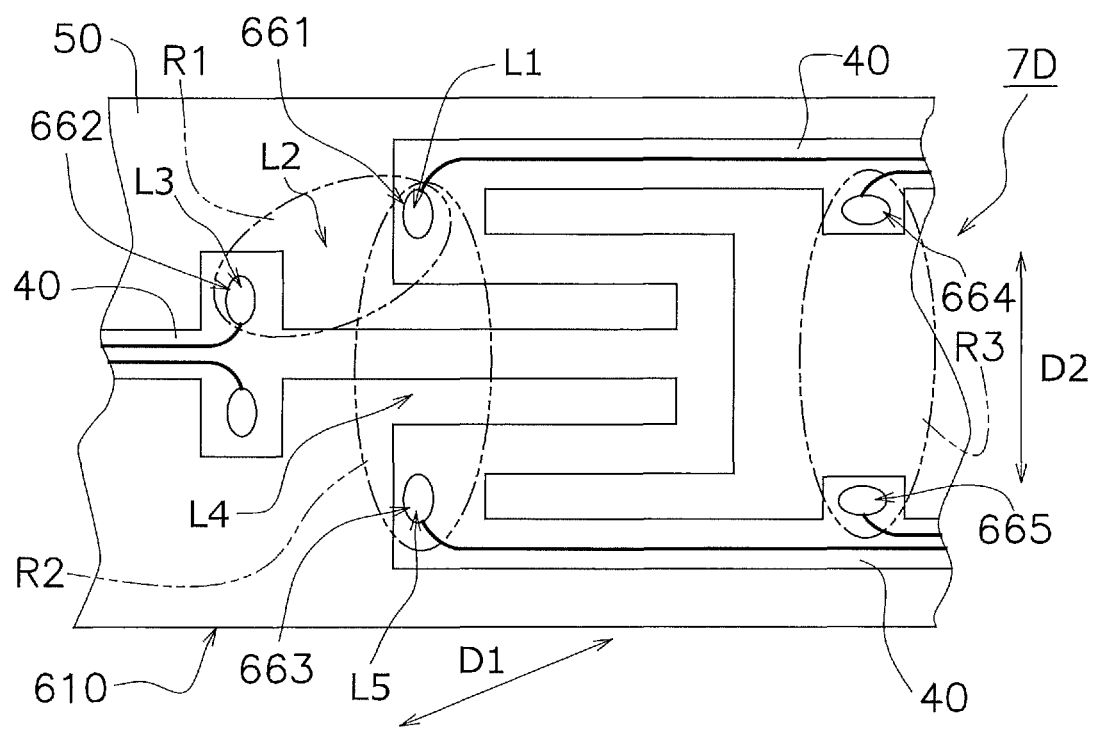
FIG. 15 is a partially enlarged plan view illustrating another example of a sheet-like device according to a modified example.

The sheet-like device 7D illustrated in FIG. 15 has a main body portion 610 having a rectangular shape in plan view. In FIG. 15, the main body portion 610 is cut out so as to omit two opposed sides. The main body portion 610 expands both in the first direction D1 and the second direction D2. When one cut out and illustrated is referred to as a right side and the other is referred to as a left side, the two rows of the first film layer 40 extend from the right side toward the left side, after U-turning twice, the respective rows join together to be one row of the first film layer 40, and the first film layer 40 extends toward the left side. In the sheet-like device 7D illustrated in FIG. 15, the first region R1 is formed in a region including a first conversion unit 661 and a second conversion unit 662. In the sheet-like device 7D, the second region R2 including the first conversion unit 661 and a third conversion unit 663 is formed. In the second region R2 of the sheet-like device 7D, a portion of only the second film layer 50 is divided by the portion where the first film layer 40 and the second film layer 50 overlap. In this way, even when the portion of only the second film layer 50 is divided by the portion where the first film layer 40 and the second film layer 50 overlap, an effect of improving the elongation of the second region R2 in the second direction D2 is provided. In the sheet-like device 7D, the third region R3 including another set of a fourth conversion unit 664 and a fifth conversion unit 665 is formed. The sheet-like device 7D having a configuration of a plurality of combined structures in which the first film layer 40 U-turns twice is easily bent in the two-dimensional direction of the plane.

(5-2) Second Modified Example

In the first embodiment and the second embodiment described above, the case where the circuit film 80 is embedded in the second film layer 50 has been described. However, the sheet-like device of the present invention may include the second film layer 50 only on any one of the front surface and the back surface of the circuit film 80.

(5-3) Third Modified Example

In the first embodiment and the second embodiment described above, the case where the decorative layers 70 are provided in the sheet-like devices 5 and 6 has been described. However, the sheet-like device of the present invention need not be provided with a decorative layer.

(5-4) Fourth Modification Example

In the first embodiment and the second embodiment described above, the case where the irregularities 71 are formed in the sheet-like devices 5 and 6 has been described. However, the sheet-like device of the present invention need not be provided with irregularities on the surface.

(5-5) Fifth Modified Example

In the first embodiment, the second embodiment, and the modified examples described above, the cases where the main body portions 10, 210, 310, 410, 510, and 610 having the band shape, the rectangular sheet shape, and the disk shape have been described. However, the shape of the main body portion of the sheet-like device according to the present invention is not limited to these shapes. For example, it may be a complex shape, such as a glove.

(6) FEATURES 6-1

As described above, in the sheet-like devices 5, 6, and 7A to 7D, the first film layer 40 has the elongation per unit length at 20° C. smaller than that of the second film layer 50. Therefore, compared with the case of directly forming the electrical circuit layer 60 on the second film layer 50 without the first film layer 40, bonding the electrical circuit layer 60 to the first film layer 40 suppresses the stretch of the portion of the second film layer 50 overlapping with the electrical circuit layer 60 by the first film layer 40. As a result, the first conversion function of the first conversion unit 61 and the second conversion function of the second conversion unit 62 of the electrical circuit layer 60 are further well protected by the first film layer 40, and the first conversion unit 61 and the second conversion unit 62 operate stably.

Further, the stress applied to the first film layer 40 is reduced by the thermoplastic elastomer of the second part L2 where the first film layer 40 is absent and the second film layer 50 is present. As a result, the electrical circuit layer 60 bonded to the first film layer 40 is protected.

Furthermore, the sheet-like device 5, 6, and 7A to 7D are configured such that the elongation per unit length of the first region R1 is greater than the elongation per unit length of the first film layer 40 alone at 20° C. The sheet-like devices 5, 6, and 7A to 7D configured in this manner allow the sheet-like devices to flexibly deform according to deformation of peripheries compared with the case where the elongation of the first region R1 is configured to be equal to or less than the elongation of the first film layer 40 alone. As a result, for example, when a wearable includes the sheet-like devices 5, 6, and 7A to 7D including the first regions R1, a wearing comfort of the wearable is improved. Note that the reason why the elongations of the first region R1 and the first film layer 40 are compared by the elongations per unit length at 20° C. is that the elongation at room temperature is important for use of the sheet-like device.

6-2

The sheet-like devices 6, 7C, and 7D described above have the third conversion units 263, 563, and 663 having the third conversion functions by the electrical circuit layers 60. The sheet-like devices 6, 7C, and 7D include the fourth parts L4, where the first film layers 40 are absent and the second film layers 50 are present, and the fifth parts L5, where the first film layers 40, the third conversion units 263, 563, and 663, and the second film layers 50 overlap. In the sheet-like device 6, the first part L1, the fourth part L4, and the fifth part L5 are arranged side by side in the order in the second direction D2 different from the first direction D1 on the inside of the surface of the second film layer 50. The second region R2 including the first part L1, the fourth part L4, and the fifth part L5 has the elongation per unit length greater than the elongation per unit length of the first film layer 40 alone when the same force is applied in the second direction D2 at 20° C. In the sheet-like device 6 configured in this manner, stability of the first to third conversion functions is improved in the second direction D2 as well, in addition to the first direction D1, and flexibility is improved.

6-3

In the sheet-like devices 5, 6, and 7A to 7D described above, the second part L2 is configured to have the substantially same thickness as the thicknesses of the first part L1 and the third part L3. The sheet-like devices 5, 6, and 7A to 7D configured in this manner do not generate a step at the boundaries between the first parts L1 and the third parts L3 and the second parts L2. Thus, stress caused by getting caught on these boundaries is prevented, and damage is less likely to occur.

6-4

The sheet-like devices 5 and 6 described above include the decorative layers 70 bonded to the second film layers 50 and representing patterns. In the sheet-like devices 5 and 6, the positional relationships between the patterns of the decorative layers 70 and the first conversion units 61 and 261 and the second conversion units 62 and 262 are fixed. As a result, when, for example, the sheet-like devices 5 and 6 are applied to the wearable, even when the sheet-like devices 5 and 6 deform due to a movement of a human body, the arranged locations of the first conversion units 61 and 261 and the second conversion units 62 and 262 can be accurately identified by the decorative layers 70. Accurately identifying the arranged locations of the first conversion units 61 and 261 and the second conversion units 62 and 262 facilitates the operations and maintenance work of the sheet-like devices 5 and 6.

6-5

The manufacturing method of the sheet-like device 5 described with reference to FIG. 5 to FIG. 8 includes the step of bonding the electrical circuit layer 60 including the first conversion unit 61 and the second conversion unit 62 to the first film layer 40 containing the thermoplastic resin as the main material to form the circuit film 80, the step of forming the second film layer 50, which contains the thermoplastic elastomer extending more than the thermoplastic resin as the main material and extends more than the first film layer 40 at 20° C., and the first elastomer film 93 including the carrier film 91a as the protective film, the step of overlapping the circuit film 80 and the first elastomer film 93 and performing the heat press, and the step of peeling the carrier film 91a.

In the step of performing heat press, while the first mold 110 is pressed against the second film layer 50 via the carrier film 91a to form the irregularities 71 on the surface of the second film layer 50, the first film layer 40 and the second film layer 50 are bonded.

Since the irregularities 71 are formed on the second film layer 50 while being protected by the carrier film 91a, deterioration of the surface of the sheet-like device 5 can be prevented. In the manufacturing method of such a sheet-like device, compared with forming the irregularities 71 on the surface of the sheet-like device 5 in a step different from the step of performing heat press on the surface of the sheet-like device 5, the number of steps of the manufacturing process can be reduced.

6-6

The manufacturing method of the sheet-like device described above includes the step of forming the decorative layer 70 on which the pattern is represented between the carrier film 91a and the second film layer 50 (see FIG. 5). The manufacturing method of the sheet-like device configured in this manner allows facilitating positioning between the arranged locations of the first conversion unit 61 and the second conversion unit 62 and the arranged location of the pattern.

Although the first embodiment, the second embodiment, and the modifications thereof of the present invention have been described above, the present invention is not limited to the above-described embodiments or modifications, and various changes are possible without departing from the gist of the invention. In particular, the plurality of embodiments and modified examples described herein can be combined arbitrarily with one another as necessary.

REFERENCE CHARACTER LIST

1 Wristband
5, 6, 7A to 7D Sheet-like device
40 First film layer
50 Second film layer
60 Electrical circuit layer
70 Decorative layer
80 Circuit film
91 Transfer film
91a Carrier film
61, 261, 361, 461, 561, 661 First conversion unit
62, 262, 362, 462, 562, 662 Second conversion unit
263, 563, 663 Third conversion unit
D1 First direction
D2 Second direction
L1 First part
L2 Second part
L3 Third part
L4 Fourth part
L5 Fifth part
R1 First region
R2 Second region

The invention claimed is:

1. A sheet-like device comprising:
a first film layer containing a thermoplastic resin as a main material;
a second film layer bonded to the first film layer, the second film layer containing a thermoplastic elastomer that extends more than the thermoplastic resin as a main material, the second film layer having an elongation per unit length greater than an elongation per unit length of the first film layer, at 20° C.;
an electrical circuit layer that includes a first conversion unit having a first conversion function and a second conversion unit having a second conversion function, the electrical circuit layer being bonded to the first film layer;
a first part where the first film layer, the first conversion unit, and the second film layer overlap;
a second part where the first film layer is absent and the second film layer is present; and
a third part where the first film layer, the second conversion unit, and the second film layer overlap, wherein
the first part, the second part, and the third part are arranged side by side in this order in a first direction on an inside of a surface of the second film layer,
the second part opens at an end portion of the first film layer and protrudes so as to separate between the first part and the third part, and
a first region including the first part, the second part, and the third part has an elongation per unit length larger than an elongation per unit length of the first film layer alone when a same force is applied in the first direction at 20° C.

2. The sheet-like device according to claim 1, wherein the electrical circuit layer includes a third conversion unit having a third conversion function,
the sheet-like device comprises:
a fourth part where the first film layer is absent and the second film layer is present; and
a fifth part where the first film layer, the third conversion unit, and the second film layer overlap,
the first part, the fourth part, and the fifth part are arranged side by side in this order in a second direction different from the first direction on the inside of the surface of the second film layer, and
a second region including the first part, the fourth part, and the fifth part has an elongation per unit length greater than the elongation per unit length of the first film layer alone when a same force is applied in the second direction.

3. The sheet-like device according to claim 1, wherein the second part has a substantially same thickness as thicknesses of the first part and the third part.

4. The sheet-like device according to claim 1, wherein the second film layer has a surface with an irregular design.

5. The sheet-like device according to claim 1, comprising a decorative layer bonded to the second film layer and representing a pattern.

* * * * *